US008129560B2

(12) United States Patent
Bowden et al.

(10) Patent No.: US 8,129,560 B2
(45) Date of Patent: Mar. 6, 2012

(54) PROCESS FOR THE SYNTHESIS OF MANDIPROPAMID AND DERIVATIVES THEREOF

(75) Inventors: Martin Charles Bowden, Huddersfield (GB); Thomas Aitcheson Clark, Huddersfield (GB); Fanny Giordano, Muenchwilen (CH); Beat Jau, Muenchwilen (CH); Hans-Dieter Schneider, Muenchwilen (CH); Gottfried Seifert, Muenchwilen (CH); Martin Zeller, Muenchwilen (CH); Dominik Faber, Muenchwilen (CH); Juerg Wiss, Muenchwilen (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 112 days.

(21) Appl. No.: 12/063,907

(22) PCT Filed: Aug. 8, 2006

(86) PCT No.: PCT/GB2006/002946
§ 371 (c)(1),
(2), (4) Date: Jun. 25, 2008

(87) PCT Pub. No.: WO2007/020381
PCT Pub. Date: Feb. 22, 2007

(65) Prior Publication Data
US 2009/0118532 A1 May 7, 2009

(30) Foreign Application Priority Data
Aug. 15, 2005 (GB) .................................. 0516705.1

(51) Int. Cl.
C07C 255/37 (2006.01)
C07C 231/02 (2006.01)
C07C 231/06 (2006.01)
C07C 43/23 (2006.01)
C07C 213/02 (2006.01)

(52) U.S. Cl. ........ 558/410; 564/170; 564/124; 564/335; 568/652

(58) Field of Classification Search ................. 558/410; 564/170, 124, 355; 568/652
See application file for complete search history.

(56) References Cited

U.S. PATENT DOCUMENTS

| 3,393,192 | A | 7/1968 | Lewis et al. | |
| 3,773,630 | A | 11/1973 | Popescu | |
| 6,683,211 | B1* | 1/2004 | Lamberth et al. | 564/175 |
| 7,105,545 | B2* | 9/2006 | Kunz et al. | 514/331 |
| 2005/0014950 | A1 | 1/2005 | Zeller et al. | |

FOREIGN PATENT DOCUMENTS

| EP | 1541557 | 6/2005 |
| FR | 2131802 | 11/1972 |
| FR | 2259160 | 8/1975 |
| GB | 1030756 | 5/1966 |
| WO | 0187822 | 11/2001 |
| WO | 03041728 | 5/2003 |
| WO | 03042166 | 5/2003 |

OTHER PUBLICATIONS

Heckmann, Mioskowski, Bhatt, Falck, "Grignard additions to alpha, beta-unsaturated dixolanones: preparation of chiral allylic alcohols and protected alpha-hydroxy aldehydes;" Tetrahedron Letters, vol. 37, No. 9, 1996, pp. 1421-1424, XP002401540.
Rudler, Parlier, Certal, Numbert, Vaissermann: "Reaction of nucleophiles with alkoxycarbene complexes of chromium: a general access to polycyclic substituted butenolides;" Tetrahedron Letters, vol. 43, 2002, pp. 5897-5899, XP002401541.
Robert, Jaguelin, Guinamat: "Syntheses d'esters ou d'acides alpha-halogenes a partir des gem dicyano expoxydes;" Tetrahedron, vol. 42, No. 8, 1986, pp. 2275-2281, XP002401542.
Enholm, Gallagher: "Free radical reactions on soluble supports from ring-opening metathesis"; Organic Letters, vol. 3, No. 21, 2001, pp. 3397-3399, XP002401543.
Mayadunne, Moad, Rizzardo: "Multiarm organic compounds for use as reversible chain-transfer agents in living radical polymerizations"; Tetrahedron Letters, vol. 43, 2002, pp. 6811-6814, XP002401544.
Moriarty, Penmasta, Awasthi, Epa, Prakash: "Reaction of [hydroxy(tosyloxy)iodo]benzene and [hydroxy(mesyloxy)iodo]benzene with trimethylsilyl enol ethers. A newgeneral method for apha-sulfonyloxylation of carbonyl compounds;" Journal of Organic Chemistry, vol. 54, 1989, pp. 1101-1104, XP002401545.
Pirrung, Michael C. "Intramolecular arene-alkyne photocycloadditions;" Journal of Organic Chemistry, 52(8), 1635-7, Coden: Joceah; ISSN: 0022-3263, 1987, XP002401546, compound 7.
Stragies, Shuster, Blechert: "A novel ruthenium-catalysed tandem diyne cycloisomerisation-cross metathesis process;" Chemical Communications, 1999, pp. 237-238, XP002401547.
Gerrits, Zumbragel, Marcus: "Analyzing the hydrocyanation reaction: chiral HPLC and the synthesis of racemic cyanohydrins", Tetrahedron, vol. 57, 2001, pp. 8691-8698, XP002416583.
Shuman Jorns: "Studies on the kinetics of cyanohydrin synthesis and cleavage by the flavoenzyme oxytrilase"; Biochimica Et Biophysica Acta, vol. 613, 1980, pp. 203-209, XP002415616. Buck: "Reduction of hydroxymandelonitriles. A new synthesis of tyramine", Journal of the Maerican Chemical Society, vol. 55, 1933, pp. 3388-3390, XP002415618.
Mori, et al: "Cyano Group Transfer of Acetone Cyanohydrin to Aldehyde Mediated by Titanium Alkoxide and Aluminum Alkyls;" Chemistry Letters, Chemical Society of Japan, Tokyo, JP, vol. 19, No. 7, 1990, pges 1171-1172, XP000151333, ISSN: 0366-7022.
Ercoli, Ruggieri: "An improved method of preparing testosterone, dihydrotestosterone and some of their esters," Journal of the American Chemical Society, vol. 75, 1953, pp. 650-653, XP002415619.
Nazarov, Akhrem, Kamernitsky: "Preparative method of the synthesis of cyanohydrins;" J. Gen. Chem. USSR (English Translation), vol. 25, 1955, pp. 1291-1295, XP009077450.

* cited by examiner

Primary Examiner — Yong Chu
(74) Attorney, Agent, or Firm — William A. Teoli, Jr.

(57) ABSTRACT

A process for the preparation of a compound of formula (I), the process comprising: (i) the reaction of a compound of formula (III), with a compound of formula (IV) to give a compound of formula (II), and (ii) the reaction of the compound of formula (II) with a leaving group, to give the compound of formula (I).

6 Claims, 1 Drawing Sheet

Figure 1: Reaction Scheme for the Preparation of Compound (I)
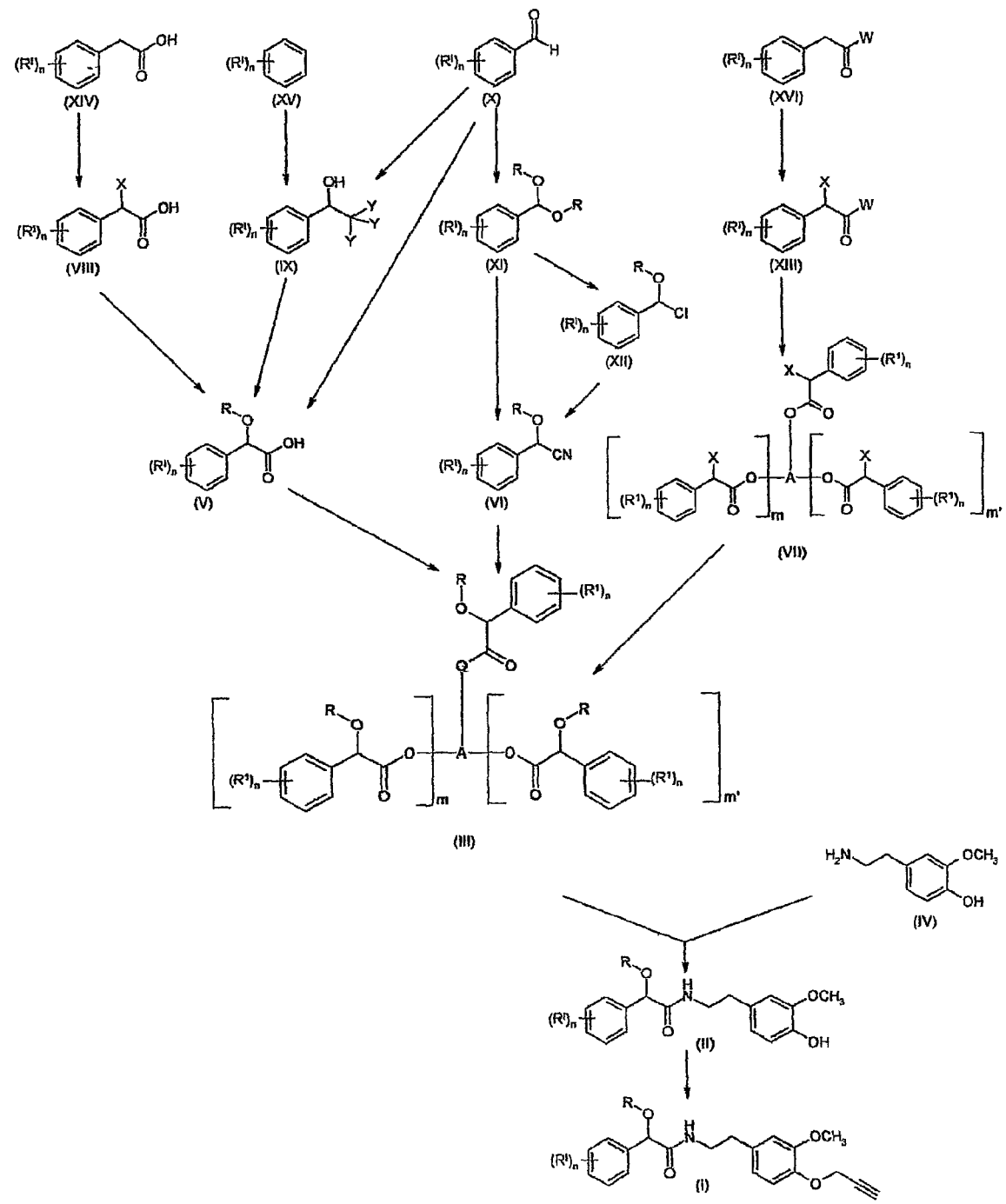

PROCESS FOR THE SYNTHESIS OF MANDIPROPAMID AND DERIVATIVES THEREOF

This application is a 371 of International Application No. PCT/GB2006/002946 filed Aug. 8, 2006, which claims priority to GB 0516705.1 filed Aug. 15, 2005, the contents of which are incorporated herein by reference.

The present invention relates to a process for the preparation of certain fungicidally active phenylpropargylether derivatives and to processes of the preparation of certain intermediates therefore.

The fungicidally active phenylpropargylether derivatives which may be prepared according to the present invention are described, for example, in WO01/87822. These fungicidally active phenylpropargylether derivatives correspond to the formula (A)

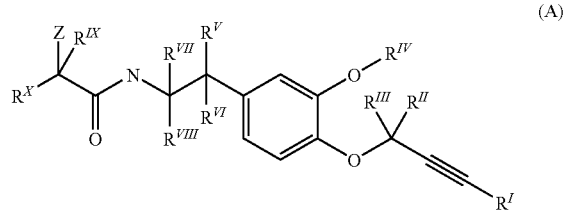

including the optical isomers thereof and mixtures of such isomers, wherein $R^I$ is hydrogen, alkyl, cycloalkyl or optionally substituted aryl;

$R^{II}$ and $R^{III}$ are each independently hydrogen or alkyl;

$R^{IV}$ is alkyl, alkenyl or alkynyl;

$R^V$, $R^{VI}$, $R^{VII}$ and $R^{VIII}$ are each independently hydrogen or alkyl;

$R^{IX}$ is hydrogen, optionally substituted alkyl, optionally substituted alkenyl or optionally substituted alkynyl;

$R^X$ is optionally substituted aryl, optionally substituted heteroaryl; and

Z is halogen, optionally substituted aryloxy, optionally substituted alkoxy, optionally substituted alkenyloxy, optionally substituted alkynyloxy, optionally substituted arylthio, optionally substituted alkylthio, optionally substituted alkenylthio, optionally substituted alkynylthio, optionally substituted alkylsulfinyl, optionally substituted alkenylsulfinyl, optionally substituted alkynylsulfinyl, optionally substituted alkylsulfonyl, optionally substituted alkenylsulfonyl or optionally substituted alkynylsulfonyl.

A variety of methods for the preparation of the compounds of the above formula (A) have been described in WO01/87822.

The present invention relates to a further alternative and preferred route to fungicidally active phenylpropargylether derivatives of formula (I)

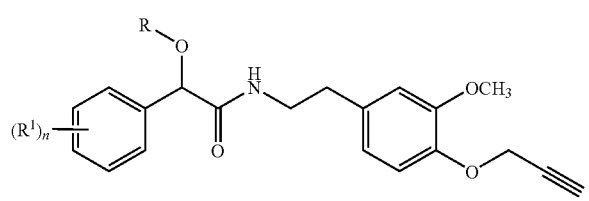

wherein:

R is an alkynyl group;

$R^1$ is alkyl, alkenyl, alkynyl, cycloalkyl, cycloalkyl-alkyl, phenyl and phenylalkyl, it being possible in turn for all of the preceding groups to carry one or more identical or different halogen atoms; alkoxy; alkenyloxy; alkynyloxy; alkoxyalkyl; haloalkoxy; alkylthio; haloalkylthio; alkylsulfonyl; formyl; alkanoyl; hydroxy; halogen; cyano; nitro; amino; alkylamino; dialkylamino; carboxyl; alkoxycarbonyl; alkenyloxycarbonyl; or alkynyloxycarbonyl; and n is an integer from 0 to 3.

The terms "alkyl", "alkenyl" or "alkynyl", either on their own or as part of another substituent, suitably contain from 1-8 (2-8 in the case of alkenyl or alkynyl) carbon atoms, more suitably from 1 to 6 (or 2-6) and preferably from 1 to 4 (or 2-4) carbon atoms.

Specific examples of R include: ethynyl, prop-1-ynyl, prop-2-ynyl, but-1-ynyl, but-2-ynyl, 1-methyl-2-butynyl, hex-1-ynyl, 1-ethyl-2-butynyl or oct-1-ynyl. Most preferred is prop-2-ynyl.

Typical examples of $R^1$ include: 4-chloro, 4-bromo, 3,4-dichloro, 4-chloro-3-fluoro, 3-chloro-4-fluoro, 4-methyl, 4-ethyl, 4-propargyloxy, 3-methyl, 4-fluoro, 4-ethenyl, 4-ethynyl, 4-propyl, 4-isopropyl, 4-tert-butyl, 4-ethoxy, 4-ethynyloxy, 4-phenyoxy, 4-methylthio, 4-methylsulfonyl, 4-cyano, 4-nitro, 4-methoxycarbonyl, 3-bromo, 3-chloro, 2-chloro, 2,4-dichloro, 3,4,5-trichloro, 3,4-difluoro, 3,4-dibromo, 3,4-dimethoxy, 3,4-dimethyl, 3-chloro-4-cyano, 4-chloro-3-cyano, 3-bromo-4-methyl, 4-methoxy-3-methyl, 3-fluoro-4-methoxy, 4-chloro-3-methyl, 4-chloro-3-trifluoromethyl, 4-bromo-3-chloro, 4-trifluoromethyl, 4-trifluoromethoxy, 4-methoxy. Suitably $R^1$ is 3-halo, 4-halo or 3,4-dihalo; preferably, 4-chloro.

Where n is either 2 or 3, the $R^1$ groups may be the same or different. Suitably, n is 1 or 2; preferably 1.

Accordingly, a first aspect of the present invention concerns a process for the preparation of a compound of formula (I) as hereinbefore defined, said process comprising:

(i) the reaction of a compound of formula (III)

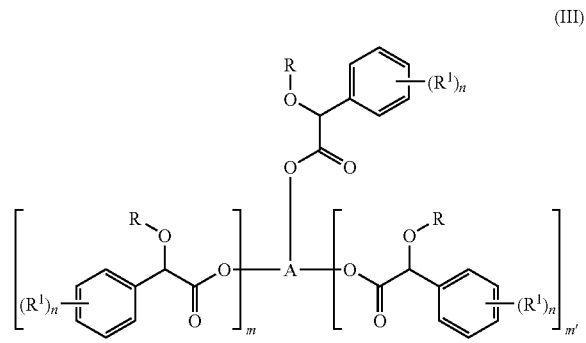

wherein R, $R^1$ and n are as hereinbefore defined;

m and m' are independently 0 or 1;

when m and m' are both 0, A is an alkyl, alkenyl or alkynyl group (suitably having up to eight carbon atoms), optionally substituted by one or more groups independently selected from halogen, hydroxy, alkoxy, $C_{1-4}$ dialkylamino or cyano;

when one of m and m' is 0 and the other is 1, A is an alkanediyl, alkenediyl or alkynediyl group containing at least two carbon atoms (and suitably having up to eight carbon atoms), optionally substituted by one or more groups independently selected from halogen, hydroxy, alkoxy, $C_{1-4}$ dialkylamino or cyano;

when m and m' are both 1, A is an alkanetriyl, alkenetriyl or alkynetriyl group containing at least three carbon atoms (and suitably having up to eight carbon atoms), optionally substituted by one or more groups independently selected from halogen, hydroxy, alkoxy, $C_{1-4}$ dialkylamino or cyano;

and wherein if the group A contains three or more carbon atoms, one or more of the carbon atoms may each optionally be replaced with an oxygen atom, provided that there is at least one carbon atom between any two oxygen atoms in the molecule, with a compound of formula (IV)

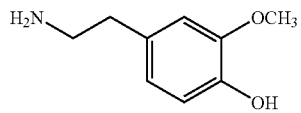

(IV)

to give a compound of formula (II)

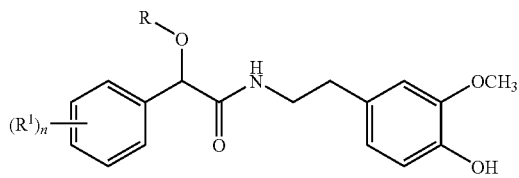

(II)

wherein R, $R^1$ and n are as hereinbefore defined, and (ii) the reaction of a compound of formula (II) with

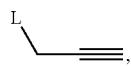

wherein L is a leaving group, to give the compound of formula (I).

By the term "alkanediyl" and "alkanetriyl", we mean an alkane group having two or three free valancies respectively (i.e. two or three missing hydrogen atoms), suitably the free valancies being on different carbon atoms.

By the term "alkenediyl" and "alkenetriyl", we mean an alkene group having two or three free valancies respectively, suitably the free valancies being on different carbon atoms.

By the term "alkynediyl" and "alkynetriyl", we mean an alkyne group having two or three free valancies respectively, suitably the free valancies being on different carbon atoms.

Suitable leaving groups L include halogens, alkylsulfonates, haloalkylsulfonates and optionally substituted arylsulfonates; and preferably L is chloro or mesylate.

Examples of compounds of formula (III) include the following:

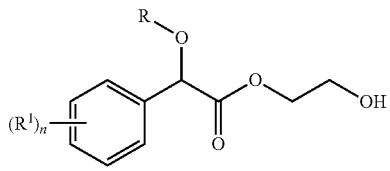

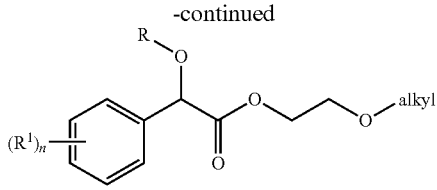

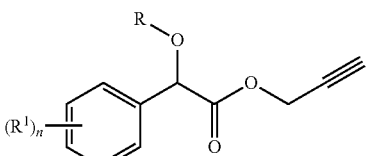

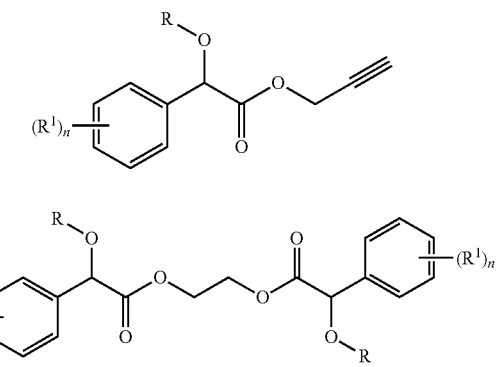

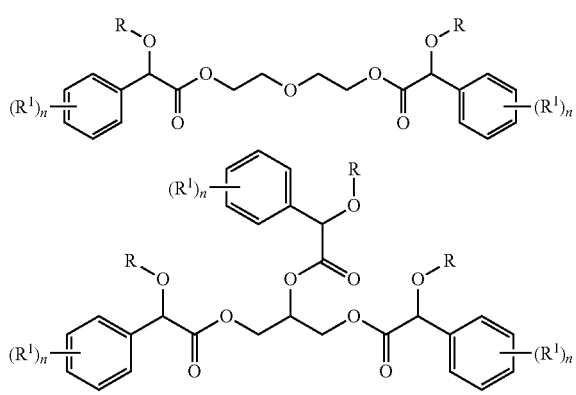

Step (i) is suitably performed in the temperature range of 50° to 150° C. The reaction can be performed in melt or in the presence of an inert solvent, for example toluene, xylene, chlorobenzene etc. The reaction temperature depends on the reactivity of the ester. To an ester of low reactivity like methylester, ethylester or benzylester, an alcohol of high reactivity like diethylaminoethanol, ethyleneglycol, triethanolamine or propargylalcohol can be added or the ester of the named alcohols directly used to decrease reaction temperature and avoid side reactions. The reaction temperature is normally between 70° C. and 120° C. At higher temperatures the formation of by-products is increased.

Step (ii) is suitably carried out in the most common polar and non-polar solvents (for example hydrocarbons e.g. toluene, xylene or chlorinated hydrocarbons e.g. chlorobenzene or ethers e.g. THF, dioxane, anisole or nitriles e.g. acetonitrile) or mixtures with water in the presence of a base like alkali metal hydroxides, alkaline earth metal hydroxides or carbonates. The solvent or solvent mixture is suitably inert against the compound (II) and the base. The base is suitably applied in a wide range, preferably in the range of 1-2 mole per mole of compound (II). The use of a phase transfer catalyst like ternary ammonium salts in the range of 0.5-10 mole % is of advantage. The reaction is suitably performed in a temperature range of 20-150° C., preferably in the range of 50-100° C.

The compound of formula (III) may be prepared from a compound of formula (V)

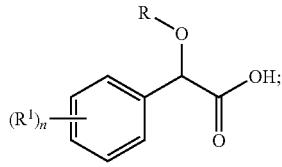

(V)

or from a compound of formula (VI)

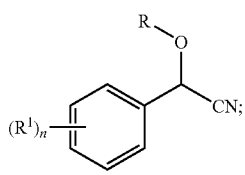

(VI)

or from a compound of formula (VII)

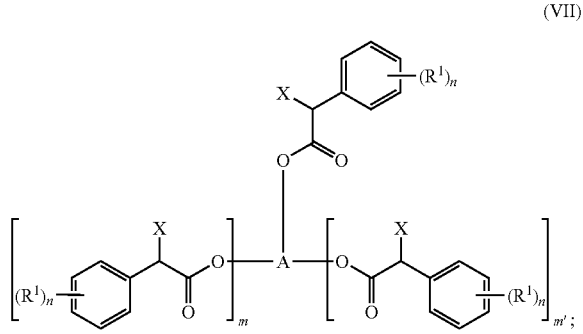

(VII)

wherein R, R¹, m, m', n and A are as hereinbefore defined and X is a leaving group. Suitable leaving groups include a halogen, such as fluoro, chloro or bromo, or alkylsulfonate or arylsulfonate.

Accordingly, a second aspect of the invention provides a process for the preparation of a compound of formula (I) as hereinbefore defined, said process comprising (i) (a) the esterification of a compound of formula (V) as hereinbefore defined;
or
(b) reaction of a compound of formula (VI) as hereinbefore defined with an alcohol of formula

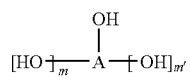

wherein A, m and m' are as hereinbefore defined; or
(c) reaction of a compound of formula (VII) as hereinbefore defined with alcohol R—OH, wherein R is as hereinbefore defined;
to give a compound of formula (III) as hereinbefore defined;
(ii) reaction of a compound of formula (III) with a compound of formula (IV) as hereinbefore defined to give a compound of formula (II) as hereinbefore defined; and (iii) reaction of a compound of formula (II) with

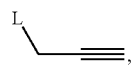

wherein L is as hereinbefore defined, to give the compound of formula (I).

Step (i)(a) is suitably performed in melt or in the presence of an inert solvent, such as toluene, xylene, chlorobenzene etc. To speed up the reaction rate the addition of a catalyst such as sulphuric acid, methanesulphonic acid or p-toluenesulphonic acid is an advantage. For high conversion, the reaction water is preferably removed by distillation or destroyed chemically, e.g. by addition of, for example, orthoformic trimethylester. The reaction is suitably carried out at a temperature of 0° C. to 150° C., preferably within the range of 50° C. to 100° C.

Step (i)(b) is suitably carried in a solvent, such as a hydrocarbon e.g. hexane, cyclohexane, methylcyclohexane or toluene; a chlorohydrocarbon e.g. dichloromethane or chlorobenzene; an ether e.g. diethylether, tert-butylmethylether, dioxane or tetrahydrofuran; or water. It is also possible to use the alcohol itself as a solvent. Mixtures of such solvents can also be used. The reaction is carried out in the presence of an acid, such as an organic or inorganic acid, like hydrogen halides e.g. hydrogen chloride, hydrogen bromide or like sulphuric acid or phosphoric acid. The reaction is suitably performed at a temperature ranging from −80° C. to the boiling temperature of the reaction mixture, preferably within the range of 0° C. to 100° C.

Step (i)(c) is suitably performed in the presence of a base, such as a trialkylamine, in the absence of water. The reaction is suitably carried out in a solvent, for example a hydrocarbon e.g. toluene, xylene or a chlorinated hydrocarbon e.g. chlorobenzene or an ether e.g. THF, dioxane, anisole or an amide e.g. DMF in presence of a base e.g. potassium carbonate, or an alcohol e.g. propargylalcohol. The reaction temperature is suitably from 0° C. to 100° C.

Steps (ii) and (iii) are carried out as described above.

Compounds of formula (V) may be prepared from a compound of formula (VIII)

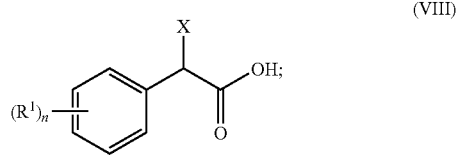

(VIII)

or from a compound of formula (IX)

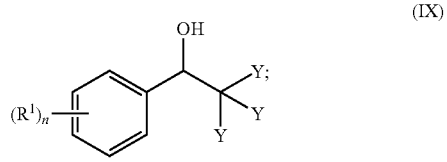

(IX)

or from a compound of formula (X)

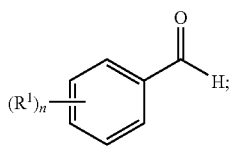

wherein R¹, n and X are as hereinbefore defined and each Y may be the same or different and is an alkoxy group or halogen; suitably $C_{1-4}$ alkoxy or halo, preferably methoxy or chloro.

Accordingly, a third aspect of the invention provides a process for the preparation of a compound of formula (I) as hereinbefore defined, said process comprising (i) (a) the reaction of a compound of formula (VIII) as hereinbefore defined with an alcohol R—OH; or (b) the reaction of a compound of formula (IX) as hereinbefore defined with an alcohol R—OH in the presence of a base; or (c) the reaction of a compound of formula (X) as hereinbefore defined with an alcohol R—OH and trihalomethane or trihaloacetic acid and in the presence of a base;

to give a compound of formula (V) as hereinbefore defined;

(ii) the esterification of a compound of formula (V) to give a compound of formula (III) as hereinbefore defined;

(iii) reaction of a compound of formula (III) with a compound of formula (IV) as hereinbefore defined to give a compound of formula (II) as hereinbefore defined; and (iv) reaction of a compound of formula (II) with

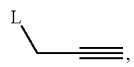

wherein L is as hereinbefore defined, to give the compound of formula (I).

Step (i)(a) is suitably carried out in the presence of a base, such as an alkali metal hydroxide or a ternary amine. The base is suitably used in a ratio of 2-10 mole per mole of compound (VIII), preferably 2.5-3.5 mole. One mole of the base is used to neutralise the carbonic acid of compound (VIII). The reaction is suitably performed at a temperature ranging from −50° C. to 120° C., preferably within the range of −10° C. to 50° C. The alcohol R—OH may be used as a solvent, or an additional solvent like an aliphatic or aromatic hydrocarbon, halogenated aromatic hydrocarbon, ketones, ethers, N-methylpyrrolidone (NMP) or dimethylsulphoxide (DMSO) may be used. Suitably, the reaction is carried out in the absence of water.

Step (i)(b) is carried out in the presence of a base, such as an alkali or alkaline earth metal hydroxide, e.g. sodium hydroxide, or potassium hydroxide, sodium- or potassium-alkoholates, e.g. sodium methoxide or nitrogen based e.g. 1,8-diazabicyclo-[5.4.0]-undec-7-ene (DBU), 1,4-diazabicyclo-[2.2.2]-octane (DABCO) (also known as triethylenediamine). Mixtures of such bases can also be used. The reaction is suitably carried out at a temperature from −80° C. to 150° C., preferably within the range of 30-100° C. The reaction is suitably carried out in a solvent, for example an organic solvent, polar or non polar, like hydrocarbons, ethers, amides, e.g. DME, Diglyme, dioxane, THF, anisole, NMP, DMSO or alcohol; the alcohol ROH may also act as the solvent.

Step (i)(c) is suitably carried out at temperatures ranging from −80° C. to 150° C., preferably within the range of 0° C. to 70° C. Trihalomethanes are derivatives of methane where three hydrogen atoms are substituted by the same or different halogens like fluorine, chlorine or bromine. Examples of such trihalomethanes are chloroform, bromoform, chloro-dibromomethane or bromo-dichloromethane. Suitable hydroxide bases are alkali or alkaline earth metal hydroxides such as sodium hydroxide or potassium hydroxide. The reaction is suitably carried out in a solvent, such as a hydrocarbon, e.g. hexane, cyclohexane, methylcyclohexane or toluene; a chlorohydrocarbon, e.g. dichloromethane or chlorobenzene; an ether e.g. diethylether, tert-butylmethylether, dioxane or tetrahydrofuran, or water. Mixtures of such solvents may also be used. The alcohol and/or trihalomethane may also be used as the solvent; in one embodiment, the alcohol R—OH is used as the solvent; in a further embodiment the trihalomethane is used as the solvent.

Steps (ii) to (iv) are carried out as described above.

The compound of formula (VI) as hereinbefore defined may be prepared from a compound of formula (XI)

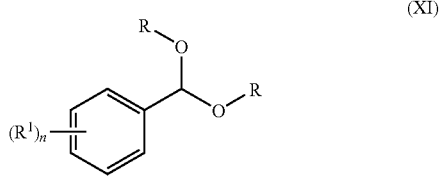

wherein R, R¹ and n are as hereinbefore, either directly or via a compound of formula (XII)

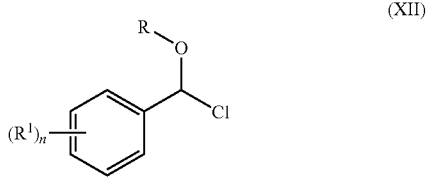

wherein R, R¹ and n are as hereinbefore.

Accordingly, a fourth aspect of the invention provides a process for the preparation of a compound of formula (I) as hereinbefore defined, said process comprising (i) (a) the reaction of a compound of formula (XI) as hereinbefore defined with a cyanating agent; or (b) (i) the reaction of a compound of formula (XI) as hereinbefore defined with a chlorinating agent to give a compound of formula (XII) as hereinbefore defined, (ii) followed by reaction of the compound of formula (XII) with a cyanating agent;

to give a compound of formula (VI) as hereinbefore defined.

(ii) reaction of a compound of formula (VI) with an alcohol of formula

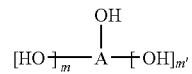

wherein m, m' and A are as hereinbefore defined to give a compound of formula (III) as hereinbefore defined;

(iii) reaction of a compound of formula (III) with a compound of formula (IV) as hereinbefore defined to give a compound of formula (II) as hereinbefore defined; and (iv) reaction of a compound of formula (II) with

wherein L is as hereinbefore defined, to give the compound of formula (I).

Step (i)(a) is suitably performed in the presence of Bronsted acids such as a strong mineral acid e.g. hydrogen chloride, hydrogen bromide or sulphuric acid, or Lewis acids, such as a group (III) compound e.g. boron trifluoride, metal salts e.g. zinc salts such as zinc (II) chloride, zinc(II)bromide, iron salts such as iron(III)chloride, cobalt salts such as cobalt (II)chloride, antimony salts such as antimony(V)chloride, scandium salts such as scandium(III)triflate, yttrium salts such as yttrium(III)triflate, indium salts such as indium(III) chloride, lanthanum salts such as lanthanum(III)triflate or bismuth salts such as bismuth(III)chloride, bismuth(III)bromide. Preferably, the acid is used in substoichiometric amounts. Suitable cyanating agents include hydrogen cyanide, cyanosilanes such as trialkysilylcyanide e.g. trimethylsilyl cyanide or like cyanohydrins. The reaction is suitably carried out in solvent, such as a hydrocarbon, e.g. hexane, cyclohexane, methylcyclohexane or toluene; a chlorohydrocarbon e.g. dichloromethane or chlorbenzene; an ether e.g. diethylether, tert-butylmethylether, dioxane or tetrahydrofuran; an amide e.g. N,N-dimethylamide, N,N-dimethylacetamide or N-methylpyrrolidone. Mixtures of solvents can also be used. The reaction is suitably performed at temperatures ranging from −80° C. to 150° C., preferably within the range of 0° C. to 70° C.

Step (i)(b)(i) is suitably carried out at a temperature ranging from −80° C. to 100° C., preferably within the range 0° to 25° C. Suitably chlorinating agents are organic chlorides such as lower alkanoyl chlorides e.g. acetyl chloride, or inorganic acid chlorides e.g. thionyl chlorides, sulfuryl chloride or phosphorus oxychloride. It is also possible to use a mixture of chlorinating agents. The reaction is carried out in a suitable solvent, such as a hydrocarbon e.g. hexane, cyclohexane, methylcyclohexane or toluene; a chlorohydrocarbon e.g. dichloromethane or chlorobenzene; an ether e.g. diethylether, tert-butylmethylether, dioxane or tetrahydrofuran. Mixtures of solvents may also be used.

Step (i)(b)(ii) is carried out in a suitable solvent such as a hydrocarbon e.g. hexane, cyclohexane, methylcyclohexane or toluene; a chlorohydrocarbon e.g. dichloromethane or chlorobenzene; an ether e.g. diethylether, tert-butylmethylether, dioxane or tetrahydrofuran; an amides e.g. N,N-dimethylamide, N,N-dimethylacetamide or N-methylpyrrolidone; or water. Mixtures of such solvents may also be used. Suitable cyanating agents include metal cyanides such as alkali or alkaline earth metal cyanides e.g. sodium cyanide or potassium cyanide. The reaction is suitably carried out at temperatures ranging from −50° C. to 100° C., preferably 0° C. to 40° C.

Steps (ii) to (iv) are carried out as described above.

The compound of formula (VII) as hereinbefore defined may be prepared from a compound of formula (XIII)

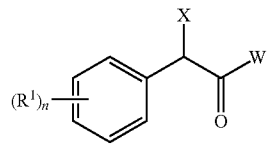

wherein $R^1$, n and X are as hereinbefore defined and W is halogen, preferably chloro.

Accordingly, a fifth aspect of the invention provides a process for the preparation of a compound of formula (I) as hereinbefore defined, said process comprising (i) reaction of a compound of formula (XIII) as hereinbefore defined with an alcohol of formula

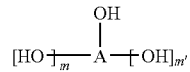

wherein A, m and m' are as hereinbefore defined to give a compound of formula (VII) as hereinbefore defined.

(ii) reaction of a compound of formula (VII) with alcohol R—OH, wherein R is as hereinbefore defined to give a compound of formula (III) as hereinbefore defined;

(iii) reaction of a compound of formula (III) with a compound of formula (IV) as hereinbefore defined to give a compound of formula (II) as hereinbefore defined; and (iv) reaction of a compound of formula (II) with

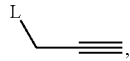

wherein L is as hereinbefore defined, to give the compound of formula (I).

Step (i) is carried out suitably in the presence of a base, such as a trialkylamine under the usual conditions for conversion of an acid chloride with an alcohol. For example, the solvent may be an alcohol like propargylalcohol and the reaction temperature is between −20° C. to 150° C., preferably within the range of 0° C. to 60° C.

Steps (ii) to (iv) are carried out as described above.

Compounds of formula (VIII) as hereinbefore defined may be prepared from a compound of formula (XIV)

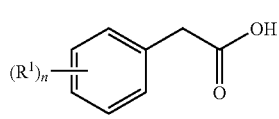

wherein $R^1$ and n are as hereinbefore defined.

Accordingly, a sixth aspect of the invention provides a process for the preparation of a compound of formula (I) as hereinbefore defined, said process comprising (i) the halogenation of a compound of formula (XIV) as hereinbefore defined to give a compound of formula (VIII) as hereinbefore defined;

(ii) the reaction of a compound of formula (VIII) with an alcohol R—OH wherein R is as hereinbefore defined to give a compound of formula (V) as hereinbefore defined;

(iii) the esterification of a compound of formula (V) to give a compound of formula (III) as hereinbefore defined;

(iv) reaction of a compound of formula (III) with a compound of formula (IV) as hereinbefore defined to give a compound of formula (II) as hereinbefore defined; and (v) reaction of a compound of formula (II) with

wherein L is as hereinbefore defined, to give the compound of formula (I).

Step (i) can be carried out in melt or in an inert solvent like acetic acid or most halogenated aromatic and aliphatic solvents. For fast reaction rates, the addition of a catalyst like red phosphor, phosphortrichloride or bromide, phosphorpentachloride or bromide, thionyl chloride or thionyl bromide, phosgene in the range of 0.01-1.0 mol per mol of compound (XIV) is recommended, preferably in the range of 0.1 to 0.5 mol. The halogenation of (XIV) can be carried out with bromine, chlorine or the corresponding succinimide in the temperature range of 50° C. to 200° C., preferably 80° C. to 150° C.

Steps (ii) to (v) may be carried out as described above.

Compounds of formula (IX) as hereinbefore defined may be prepared from a compound of formula (X) as hereinbefore defined or from a compound of formula (XV)

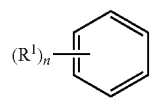

(XV)

wherein $R^1$ and n are as hereinbefore defined.

Accordingly, a seventh aspect of the invention provides a process for the preparation of a compound of formula (I) as hereinbefore defined, said process comprising:

(i) (a) the addition of a trihalomethane-anion to a compound of formula (X) as hereinbefore defined; or (b) the addition of a trihaloacetaldehyde to a compound of formula (XV) as hereinbefore defined;

to give a compound of formula (IX) as hereinbefore defined;

(ii) the reaction of a compound of formula (IX) with an alcohol R—OH with trihalomethane and in the presence of a base to give a compound of formula (V) as hereinbefore defined;

(iii) the esterification of a compound of formula (V) to give a compound of formula (III) as hereinbefore defined;

(iv) reaction of a compound of formula (III) with a compound of formula (IV) as hereinbefore defined to give a compound of formula (II) as hereinbefore defined; and (v) reaction of a compound of formula (II) with

wherein L is as hereinbefore defined, to give the compound of formula (I).

Step (i)(a) is suitably carried out in a solvent, such as a hydrocarbon, e.g. hexane, cyclohexane, methylcyclohexane or toluene; a chlorohydrocarbon, e.g. dichloromethane or chlorobenzene; an ether e.g. diethylether, tert-butylmethylether, dioxane or tetrahydrofuran; an amide e.g. N,N-dimethylformamide, N,N-dimethylacetamide or N-methylpyrrolidone; or water. Mixtures of solvents may also be used. Trihalomethanes are derivative of methane where three hydrogens are substituted by the same of different halogens like fluorine, chlorine or bromine. Examples of such trihalomethanes are chloroform, bromoform, chlorodibromomethane or bromodichloromethane. It is also possible to use alkali or alkaline earth metal salts or trihalomethane carboxylic acids in the presence of the corresponding trihalomethane carboxylic acid such as trichloroacetic acid sodium salt or trichloroacetic acid potassium salt in the presence of trichloroacetic acid. The reaction is suitably carried out at temperatures ranging from –80° C. to 150° C., preferably within the range 0 to 70° C.

Step (i)(b) is carried out in suitable solvent, such as carbon disulfide; a chlorohydrocarbon e.g. dichloromethane or chloroform; an aromatic compound e.g. chlorobenzene, dichlorobenzene, trichlorobenzene, nitrobenzene; an ether, e.g. diethylether, tert-butylmethylether, dioxane or tetrahydrofuran. Mixtures of solvents may also be used. Trihaloacetaldehydes are derivatives of acetaldehyde where three hydrogen atoms are substituted by the same or different halogen atoms, such as fluorine, chlorine or bromine. Examples of such trihaloacetaldehydes are trichloroacetaldehyde, tribromoacetaldehyde, chlorodibromoacetaldehyde or bromodichloroacetaldehyde. The reaction is suitably carried out at temperatures ranging from –80° C. to 150° C., preferably within the range of –10° C. to 70° C.

Steps (ii) to (v) are carried out as described above.

Compounds of formula (XI) as hereinbefore defined are prepared from compounds of formula (X) as hereinbefore defined.

Accordingly, an eighth aspect of the present invention provides a process for the preparation of a compound of formula (I) as hereinbefore defined, said process comprising:

(i) the reaction of a compound of formula (X) as hereinbefore defined with an alcohol R—OH in the presence of an acid to give a compound of formula (XI) as hereinbefore defined;

(ii) (a) the reaction of a compound of formula (XI) with a cyanating agent; or (b) (i) the reaction of a compound of formula (XI) with a chlorinating agent to give a compound of formula (XII) as hereinbefore defined, followed by (ii) reaction of the compound of formula (XII) with a cyanating agent;

to give a compound of formula (VI) as hereinbefore defined.

(iii) reaction of a compound of formula (VI) with an alcohol of formula

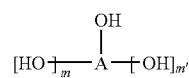

wherein A, m and m' are as hereinbefore defined to give a compound of formula (III) as hereinbefore defined;

(iv) reaction of a compound of formula (III) with a compound of formula (IV) as hereinbefore defined to give a compound of formula (II) as hereinbefore defined; and (v) reaction of a compound of formula (II) with

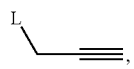

wherein L is as hereinbefore defined, to give the compound of formula (I).

Step (i) is carried out in the presence of a suitable solvent such as a hydrocarbon, e.g. hexane, cyclohexane, methylcyclohexane or toluene; a chlorohydrocarbon, e.g. dichloromethane or chlorobenzene; an ether e.g. diethylether, tert-butylmethylether, dioxane or tetrahydrofuran. In a preferred embodiment, the alcohol R—OH is used as a solvent. Mixtures of solvents may also be used. The reaction is performed in the presence of an acid, such as a Bronsted acid, for example strong mineral acids e.g. hydrogen chloride, hydrogen bromide or sulphuric acid; a Lewis acid, such as a group (III) compound e.g. boron trifluoride; a metal salt, for example zinc salts e.g. zinc(II)chloride, zinc(II)bromide, iron salts e.g. iron(III)chloride, cobalt salts e.g. cobalt(II)chloride, antimony salts e.g. antimony(V)chloride, scandium salts e.g. scandium(III)triflate, yttrium salts e.g. yttrium(III)triflate, indium salts e.g. indium(III)chloride, lanthanum salts e.g. lanthanum(III)triflate or bismuth salts e.g. bismuth(III)chloride, bismuth(III)bromide. Preferably the acid is used in substoichiometric amounts. The reaction may also be performed in the presence of orthoester, such as orthoester of lower alkylcarboxylic acids and lower alkylalcohols such as trimethyl orthoformate, trimethyl orthoacetate, triethyl orthoformate or triethyl orthoacetate. Preferably, an orthoester is used where the reaction products (ester and alcohol) can be removed from the reaction mixture by distillation. The reaction is suitably carried out at temperatures ranging from −80° C. to the boiling point of the reaction mixture, preferably within the range of 0° C. to 100° C.

Steps (ii) to (v) are carried out as described above.

Compounds of formula (XIII) as hereinbefore defined may be prepared from compounds of formula (XVI)

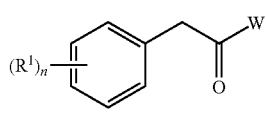
(XVI)

wherein $R^1$, W and n are as hereinbefore defined.

Accordingly, a ninth aspect of the invention provides a process for the preparation of a compound of formula (I) as hereinbefore defined said process comprising:

(i) the halogenation of a compound of formula (XVI) as hereinbefore defined to give a compound of formula (XIII) as hereinbefore defined;

(ii) reaction of a compound of formula (XIII) with an alcohol of formula

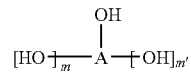

wherein A, m and m' are as hereinbefore defined to give a compound of formula (VII) as hereinbefore defined.

(iii) reaction of a compound of formula (VII) with alcohol R—OH, wherein R is as hereinbefore defined to give a compound of formula (III) as hereinbefore defined;

(iv) reaction of a compound of formula (III) with a compound of formula (IV) as hereinbefore defined to give a compound of formula (II) as hereinbefore defined; and (v) reaction of a compound of formula (II) with

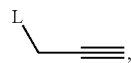

wherein L is as hereinbefore defined, to give the compound of formula (I).

Step (i) is carried out as described in Canadian Patent 967978 in a melt or an inert solvent such as chlorinated hydrocarbons or chlorinated aromatic in the temperature range of 50° C. to 150° C.

Step (ii) to (v) are carried out as described above.

Compounds of formulae (IV), (X), (XIV), (XV) and (XVI) are known in the art and processes for their preparation are readily available to the skilled person.

Alternatively, compounds of formula (IV) may be prepared by a novel process according to the following reaction scheme:

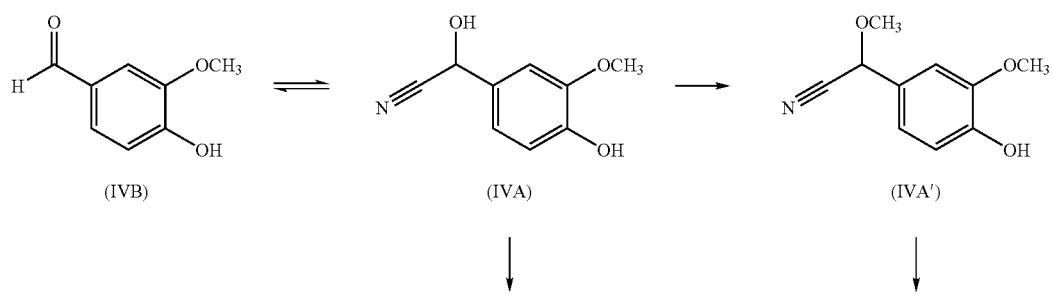

-continued (IVA″) → (IV)

The prior art processes for preparing compounds of formula (IVA) generate a considerable quantity of aqueous waste and/or use expensive catalysts; the aqueous waste generated needs to be treated (destruction of cyanide with bleach or hydrogen peroxide), which is very expensive and generates waste waters, which still contain toxic components.

In the above scheme, compound (IVB) is converted to compound (IVA) by one of the following process:

(i) reacting compound (IVB) with a cyanide e.g. sodium or potassium cyanide (preferably with a slight excess) at a pH of between 5 and 9, preferably between 6 and 7 and subsequently reducing the pH to below 3 or (ii) reacting compound (IVB) with HCN in an organic or aqueous solvent; or (iii) reacting compound (IVB) with acetone cyanohydrin in the presence of a catalytic amount of cyanide or an ordinary base.

Compound (IVA) is then reduced using $H_2$/Pd—C and $H_2SO_4$/MeOH. In a first method, the $H_2$/Pd—C and $H_2SO_4$/MeOH are added, together and the process proceeds via intermediate (IVA″); in a second method the $H_2SO_4$/MeOH is added first to give intermediate (IVA′), followed by reduction using $H_2$/Pd—C.

Thus, a further embodiment of the invention provides a process for the preparation of compound (IV), said process comprising:

(i) the reaction of compound (IVB)

(a) with a cyanide e.g. sodium or potassium cyanide (preferably with a slight excess) at a pH of between 5 and 9, preferably between 6 and 7 and subsequently reducing the pH to below 3 or (b) with HCN in an organic or aqueous solvent; or (c) with acetone cyanohydrin in the presence of a catalytic amount of cyanide or an ordinary base;

to give compound (IVA), and (ii) the reduction of compound (IVA) using $H_2$/Pd—C and $H_2SO_4$/MeOH via intermediate (IVA′) or (IVA″) and its tautomers to give compound (IV).

Intermediates (IVA′) as well as (IVA″) and its "hydroxyenamine" tautomer are also novel and form a further aspect of the invention.

The preparation of a compound of formula (II) from a compound of formula (III) is also a novel and inventive process and accordingly provides a further aspect of the present invention.

Many of the intermediates of formula (II), (III), (V), (VI), (VII), (XI) or (XII), in particular where $R^1$ is halo e.g. 4-chloro, are also novel and accordingly individually provide a further aspect of the invention.

A reaction scheme depicting all the various reactions described above is given in FIG. 1.

The invention will now be further illustrated with reference to the following examples:

EXAMPLE 1

1-(Bis-prop-2-ynyloxy-methyl)-4-chloro-benzene (4-Chloro-benzaldehyde-di-propargylacetal) (Compound of formula XI)

4-Chloro-benzaldehyde (14.3 g) is added to propargyl alcohol (56.6 g) and concentrated hydrochloric acid (0.1 ml). The reaction mixture is stirred and heated to 80° C. Then trimethyl orthoformate (11.9 g) is added continuously over 1 hour. The reaction mixture is stirred at 85° C. for 5 hours and some material is distilled off. The reaction mixture is cooled to room temperature. Tert-butyl methyl ether (200 ml) is added. The organic phase is washed with 40% sodium hydrogensulfite solution (2×200 ml), dried (sodium sulfate) and evaporated. 1-(Bis-prop-2-ynyloxy-methyl)-4-chloro-benzene (18.8 g) is obtained as colourless oil.

$^1$H-NMR (CDCl$_3$) δ (ppm): 2.45 (t, 2H); 4.15 (dd, 2H); 4.3 (dd, 2H); 5.85 (s, 1H); 7.35 (d, 2H); 7.45 (d, 2H).

EXAMPLE 2

1-Chloro-4-(chloro-prop-2-ynyloxy-methyl-benzene (Compound of formula XII)

1-(Bis-prop-2-ynyloxy-methyl)-4-chloro-benzene (11.7 g) is added to acetyl chloride (19.9 g) and thionyl chloride (0.2 ml) over 1 hour. The temperature is maintained at 20° C. by occasionally cooling. The reaction mixture is stirred at room temperature for 20 hours. The reaction mixture is evaporated at 20-30° C. using vacuum. 1-Chloro-4-(chloro-prop-2-ynyloxy-methyl)-benzene (13.4 g) is obtained as oil.

¹H-NMR (CDCl₃) δ (ppm): 2.6 (t, 1H); 4.6 (d, 2H); 6.75 (s, 1H); 7.35 (d, 2H); 7.45 (d, 2H).

EXAMPLE 3

(4-Chloro-phenyl)-prop-2-ynyloxy-acetonitrile
(Compound of formula VI)

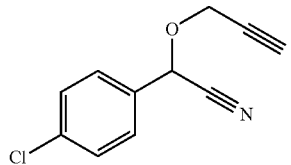

1-Chloro-4-(chloro-prop-2-ynyloxy-methyl)-benzene (13.0 g) is added to sodium cyanide (3.1 g) in N,N-dimethylformamide (40 ml) over 2 hours at room temperature. The reaction mixture is stirred at room temperature for 3 hours and then poured into water (200 ml), which contained sodium hydroxide (4 g). The aqueous phase is extracted with tert butyl methyl ether (2×200 ml). The organic phases are washed with water (2×50 ml), combined, dried (sodium sulfate) and evaporated. (4-Chloro-phenyl)-prop-2-ynyloxy-acetonitrile (9.2 g) is obtained which is purified by flash column chromatography on silica gel using ethyl acetate/hexane as eluant.

¹H-NMR (CDCl₃) δ (ppm): 2.6 (t, 1H); 4.4 (d, 2H); 5.5 (s, 1H); 7.4-7.5 (m, 4H).

EXAMPLE 4

(4-Chloro-phenyl)-prop-2-ynyloxy-acetonitrile
(Compound of formula VI)

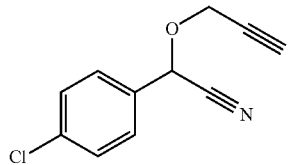

Under an atmosphere of nitrogen, trimethylsilyl cyanide (3.1 g) is added to bismuth (III)bromide (0.22 g) and 1-(bis-prop-2-ynyloxy-methyl)-4-chloro-benzene (6.7 g) in dichloromethane (50 ml) at room temperature. The reaction mixture is stirred for 48 hours at room temperature and then poured into 0.5 M hydrochloric acid (50 ml). The organic phase is separated, dried (magnesium sulfate) and evaporated. Crude (4-chloro-phenyl)-prop-2-ynyloxy-acetonitrile (3.7 g) is obtained as oil.

¹H-NMR (CDCl₃) δ (ppm): 2.6 (t, 1H); 4.4 (d, 2H); 5.5 (s, 1H); 7.4-7.5 (m, 4H).

EXAMPLE 5

(4-Chloro-phenyl)-prop-2-ynyloxy-acetic acid methyl ester (Compound of formula III)

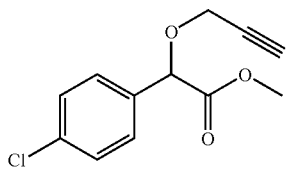

A mixture of (4-chloro-phenyl)-prop-2-ynyloxy-acetonitrile (6.4 g) and 37% hydrochloric acid (12.6 g) in methanol (40 ml) is heated to reflux for 16 hours. The reaction mixture is cooled to room temperature and water (25 ml) is added. The aqueous phase is extracted with ethyl acetate (2×25 ml). The organic phases are combined, washed with water (1×25 ml), dried (sodium sulfate) and evaporated. Crude (4-chloro-phenyl)-prop-2-ynyloxy-acetic acid methyl ester is obtained as oil.

¹H-NMR (CDCl₃) δ (ppm): 2.5 (t, 1H); 3.7 (s, 3H); 4.15 (dd, 1H); 4.3 (dd, 1H); 5.2 (s, 1H); 7.3-7.5 (m, 4H).

EXAMPLE 6

(4-Chloro-phenyl)prop-2-ynyloxy-acetic acid
(Compound of formula V)

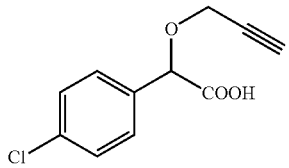

a) A mixture of potassium hydroxide (23.4 g, assay 90%) in propargyl alcohol (70 ml) is added to 4-chloro-benzaldehyde (7.2 g) and chloroform (13.4 g) in propargyl alcohol (10 ml) over 5 hours at 50° C. The reaction mixture is stirred at 50° C. for additional 3 hours. After cooling to room temperature water (150 ml) is added. The resulting mixture is extracted with tert butyl methyl ether (150 ml). The organic phase is again extracted with 4M potassium hydroxide (50 ml). The aqueous alkaline extracts are combined and made acidic (pH<3) by addition of concentrated hydrochloric acid. The aqueous phase is extracted with tert butyl methyl ether (2×150 ml). The organic phases are combined, extracted with water (1×100 ml), dried (magnesium sulfate) and evaporated. (4-Chloro-phenyl)-prop-2-ynyloxy-acetic acid (7.7 g) is obtained as oil, which solidifies on standing.

b) 4-Chloro-benzaldehyde (7.2 g) in propargyl alcohol (15 ml) is heated to 50° C. A mixture of potassium hydroxide (31.2 g, assay 90%) in propargyl alcohol (150 ml) as well as a mixture of bromoform (13 g) in propargylalcohol (15 ml) are added simultaneously over 1 hour at 50° C. The reaction mixture is stirred at 50° C. for additional 5 hours. After cooling to room temperature water (150 ml) is added. The resulting mixture is extracted with tert butyl methyl ether (150 ml). The organic phase is again extracted with 4M potassium hydroxide (50 ml). The aqueous alkaline extracts are combined and made acidic (pH<3) by addition of concentrated hydrochloric acid. The aqueous phase is extracted with tert butyl methyl ether (2×150 ml). The organic phases are combined, extracted with water (1×100 ml), dried (magnesium sulfate) and evaporated. (4-Chloro-phenyl)-prop-2-ynyloxy-acetic acid (10.4 g) is obtained as oil, which solidifies on standing.

$^1$H-NMR (CDCl$_3$) δ (ppm): 2.5 (t, 1H); 4.15 (dd, 1H); 4.3 (dd, 1H); 5.2 (s, 1H); 7.3-7.5 (m, 4H); 7.2-9.5 (s, broad, 1H).

EXAMPLE 7

2,2,2-Trichloro-1-(4-chloro-phenyl)-ethanol
(Compound of formula IX)

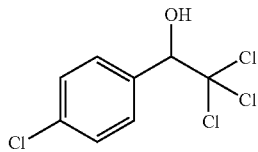

A mixture of 4-chloro-benzaldehyde (35.5 g) and trichloro acetic acid (61.5 g) in N,N-dimethylformamide (200 ml) is stirred at 30-35° C. Trichloro acetic acid sodium salt (71.5 g) is added in portions over 20 minutes. Occasionally cooling is necessary. The reaction mixture is stirred at 30° C. for 2 hours. Towards the end it becomes viscous and additional N,N-dimethylformamide (150 ml) is charged. The reaction mixture is poured into water (700 ml). The aqueous phase is extracted with ethyl acetate (600 ml). The organic phase is separated, washed with water (300 ml), dried (magnesium sulfate) and evaporated. 2,2,2-Trichloro-1-(4-chloro-phenyl)-ethanol is obtained as oil.

$^1$H-NMR (CDCl$_3$) δ (ppm): 4.1 (s, broad, 1H); 5.2 (s, 1H); 7.3 (d, 2H); 7.55 (d, 2H).

EXAMPLE 8

2,2,2-Trichloro-1-(4-chloro-phenyl)-ethanol
(Compound of formula IX)

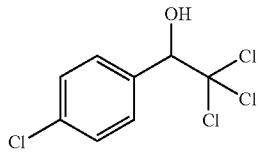

A mixture of chlorobenzene (1400 g) and trichloro-acetaldehyde (384 g) is stirred at 0-2° C. Aluminium chloride (274 g) is added in portions over 110 minutes at the same temperature. Occasionally cooling is necessary. The reaction mixture is stirred at 0-5° C. for 5 hours. The reaction mixture is poured into ice/water (3000 g). The organic phase is separated, washed three times with water (500 g each), dried (sodium sulfate) and evaporated. 2,2,2-Trichloro-1-(4-chloro-phenyl)-ethanol is obtained as oil.

$^1$H-NMR (CDCl$_3$) δ (ppm): 4.1 (s, broad, 1H); 5.2 (s, 1H); 7.3 (d, 2H); 7.55 (d, 2H).

EXAMPLE 9

(4-Chloro-phenyl)-prop-2-ynyloxy-acetic acid
(Compound of formula V)

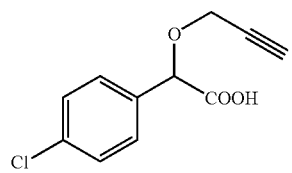

To a mixture of propargyl alcohol (300 g) and 2,2,2-Trichloro-1-(4-chloro-phenyl)-ethanol (501 g) is added a 15% solution (1820 g) of sodium hydroxide and propargyl alcohol over three hours at 70-75° C. Occasionally cooling is necessary. The reaction mixture is stirred at the same temperature for 3 hours. After the most part of the solvent is distilled off, the residue is cooled to room temperature and water/ethylacetate is added. The organic phase is again extracted with 2M sodium hydroxide (50 ml). The combined aqueous alkaline extracts are acidified (pH<3) by addition of concentrated hydrochloric acid. The aqueous phase is extracted twice with ethylacetate. The organic phases are combined, extracted with water, dried (sodium sulfate) and evaporated. (4-Chloro-phenyl)-prop-2-ynyloxy-acetic acid (10.4 g) is obtained as oil.

$^1$H-NMR (CDCl$_3$) δ (ppm): 2.5 (t, 1H); 4.15 (dd, 1H); 4.3 (dd, 1H); 5.2 (s, 1H); 7.3-7.5 (m, 4H); 7.2-9.5 (s, broad, 1H).

EXAMPLE 10

2-(4-Chloro-phenyl)-N-[2-(3-methoxy-4-prop-2-ynyloxy-phenyl)-ethyl]-2-prop-2-ynyloxyacetamide
(Compound of formula I)

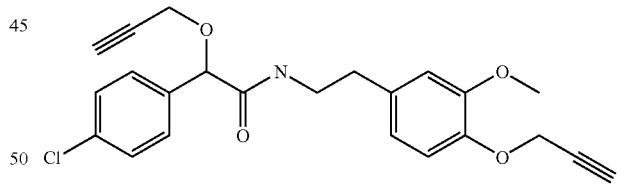

To a solution of 1 mol 2-(4-Chloro-phenyl)-N-[2-(4-hydroxy-3-methoxy-phenyl)-ethyl]-2-prop-2-ynyloxyacetamide in 500 ml toluene, 207 g potassium carbonate (1.5 mole) and 10 g tetrabutylammonium bromide are added. The mixture is heated to 90° C. and 1.4 mole propargyl chloride as a 35% solution in toluene is added over 30 minutes. After 3 hours the conversion of 2-(4-Chloro-phenyl)-N-[2-(4-hydroxy-3-methoxy-phenyl)-ethyl]-2-prop-2-ynyloxyacetamide is complete. To dissolve the salts 500 ml water are added and separated from the toluene product phase. The toluene is completely evaporated at 80° C./20 mbar and replaced by methanol. The product 2-(4-Chloro-phenyl)-N-[2-(3-methoxy-4-prop-2-ynyloxy-phenyl)-ethyl]-2-prop-2-ynyloxyacetamide is crystallized from solution by cooling down to 0° C., filtered and washed with 200 ml methanol of 0° C. The product is dried at 50° C. under vacuum. 315 g of 2-(4-Chloro-phenyl)-N-[2-(3-methoxy-4-prop-2-ynyloxy-phenyl)-ethyl]-2-prop-2-ynyloxyacetamide are obtained with a LC purity of 98%. Melting point=94-96° C.

EXAMPLE 11

2-(4-Chloro-phenyl)-N-[2-(4-hydroxy-3-methoxy-phenyl)-ethyl]-2-prop-2-ynyloxy-acetamide (Compound of formula II)

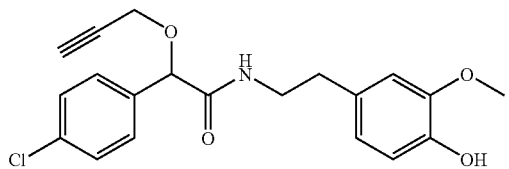

To a solution of 1 mol (4-Chloro-phenyl)-prop-2-ynyloxy-acetic acid 2-[2-(4-chloro-phenyl)-2-prop-2-ynyloxy-acetoxy]-ethyl ester ("glycolester") in 500 g chlorobenzene (obtained from 1 mol of (4-Chloro-phenyl)-prop-2-ynyloxy-acetic acid), 1.05 mol 4-(2-amino-ethyl)-2-methoxy-phenol ("AE-phenol") and 0.3 mol diethylaminoethanol are added. The reaction mixture is heated to 90-100° C. and the chlorobenzene is distilled off under vacuum. After stirring for 3-4 hours at 90-100° C. the conversion of glycolester is complete. 500 g toluene and 250 ml water are added. After stirring for 5 minutes at 50-70° C. the aqueous phase is separated. To the toluene phase 250 ml water are added and the pH is adjusted to 0.5-1.0 with aqueous hydrochloric acid 32% to remove excess AE-phenol and dimethylaminoethanol. The aqueous phase is separated and to the toluene phase of 2-(4-Chloro-phenyl)-N-[2-(4-hydroxy-3-methoxy-phenyl)-ethyl]-2-prop-2-ynyloxy-acetamide, 20 g Prolith rapid (bleaching agent) is optionally added, stirred for 30 minutes at 50-60° C. and then filtered. The toluene filtrate containing the product 2-(4-Chloro-phenyl)-N-[2-(4-hydroxy-3-methoxy-phenyl)-ethyl]-2-prop-2-ynyloxy-acetamide in 92% yield (by LC analysis) is directly used in the next step. 2-(4-Chloro-phenyl)-N-[2-(4-hydroxy-3-methoxy-phenyl)-ethyl]-2-prop-2-ynyloxy-acetamide can be partly isolated by crystallisation/filtration from the toluene solution at −10° C. in a yield of 224 g (60% of theory based on glycolester). Melting point=93-95° C.

EXAMPLE 11a 2-(4-Chloro-phenyl)-N-[2-(4-hydroxy-3-methoxy-phenyl)-ethyl]-2-prop-2-ynyloxy-acetamide (Compound of formula II)

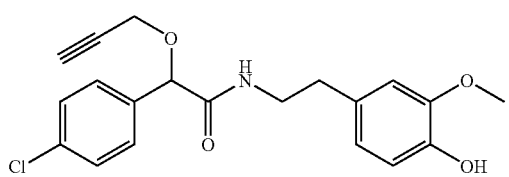

To a solution of 1 mol (4-Chloro-phenyl)-prop-2-ynyloxy-acetic acid 2-[2-(4-chloro-phenyl)-2-prop-2-ynyloxy-acetoxy]-ethyl ester ("glycolester") in 500 g chlorobenzene (obtained from 1 mol of (4-Chloro-phenyl)-prop-2-ynyloxy-acetic acid), 1.05 mol 4-(2-amino-ethyl)-2-methoxy-phenol ("AE-phenol") and 0.3 mol diethylaminoethanol are added. The reaction mixture is heated to 90°-100° C. and the chlorobenzene is distilled off under vacuum. After stirring for 3-4 hours at 90°-100° C. the conversion of glycolester is complete. 500 g toluene and 250 ml water are added. After stirring for 5 minutes at 50°-70° C. the aqueous phase is separated. To the toluene phase 250 ml water are added and the pH is adjusted to 0.5-1.0 with aqueous hydrochloric acid 32% to remove excess AE-phenol and dimethylaminoethanol. The aqueous phase is separated and to the toluene phase of 2-(4-Chloro-phenyl)-N-[2-(4-hydroxy-3-methoxy-phenyl)-ethyl]-2-prop-2-ynyloxy-acetamide, 20 g Prolith rapid (bleaching agent) is optionally added, stirred for 30 minutes at 50°-60° C. and then filtered. To the toluene filtrate, a 12% $Na_2CO_3$ solution or 50% $K_2CO_3$ solution is added and the pH adjusted to 8.5-10.5 to eliminate by-products with acid moieties. The organic layer containing the product 2-(4-Chloro-phenyl)-N-[2-(4-hydroxy-3-methoxy-phenyl)-ethyl]-2-prop-2-ynyloxy-acetamide in 92% yield (by LC analysis) is directly used in the next step. 2-(4-Chloro-phenyl)-N-[2-(4-hydroxy-3-methoxy-phenyl)-ethyl]-2-prop-2-ynyloxy-acetamide can be partly isolated by crystallisation/filtration from the toluene solution at −10° C. in a yield of 224 g (60% of theory based on glycolester). Melting point=93°-95° C.

EXAMPLE 12

(4-Chloro-phenyl)-prop-2-ynyloxy-acetic acid 2-hydroxy ethyl or (4-Chloro-phenyl)-prop-2-ynyloxy-acetic acid 2-[2-(4-chloro-phenyl)-2-prop-2-ynyloxy-acetoxy]-ethyl ester (Compound of formula III)

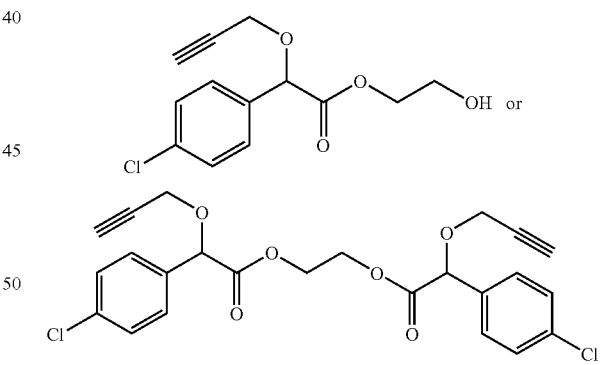

To a solution of (4-Chloro-phenyl)-prop-2-ynyloxy-acetic acid (1 mol) in 600 g chlorobenzene 0.75 mol ethylenglycol and 4 g p-toluenesulfonic acid are added and heated to under vacuum to reflux at 90°-100° C. Reaction water is separated from the condensate and the chlorobenzene returned to the reactor. After 1 hour the esterification is complete. At the end 100 g chlorobenzene are distilled off. The reaction mixture contains a mixture of mono- and di-esters of the ethylenglycol which are directly converted to 2-(4-Chloro-phenyl)-N-[2-(4-hydroxy-3-methoxy-phenyl)-ethyl]-2-prop-2-ynyloxy-acetamide in the next step (Example 11) without isolation.

EXAMPLE 13

(4-Chloro-phenyl)-prop-2-ynyloxy-acetic acid methyl ester Compound of formula (III)

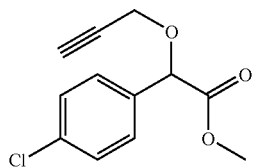

To a solution of (4-chlorophenyl)-prop-2-ynyloxy acetic acid (1 mol) in 500 g chlorobenzene 2 mole methanol, 1 mol orthoformic acid trimethylester and 4 g p-toluenesulfonic acid are added. The mixture is heated to 50-60° C. and kept for 2-3 hours until the esterification of (4-chlorophenyl)-prop-2-ynyloxy acetic acid is complete. The low boilers like methanol and methylformate are distilled off under vacuum at 50-60° C. The solution of the "methylester" in chlorobenzene can directly be converted to II in the next step without isolation. When the solvent is distilled off under vacuum, 245 g oil are obtained, containing 236 g (4-chlorophenyl)-prop-2-ynyloxy acetic acid methyl ester determined by LC analysis.

$^1$H-NMR (CDCl$_3$) δ (ppm): 2.5 (s, HC≡); 3.7 (s, OCH$_3$) (4.2+4.3 (2d, CH$_2$); 5.2 (1s, CH); 7.35 (4H, Ar)

EXAMPLE 14

(4-Chloro-phenyl)-prop-2-ynyloxy-acetic acid (Compound of formula V)

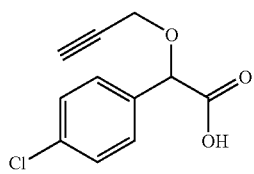

In a stirred reactor 500 g chlorobenzene, 177-187 g potassium hydroxide 90-95% (3.0 mole) and 112 g propargyl alcohol (2 mole) are pre-charged. At 15-20° C. a solution of 1 mol bromo-(4-chloro-phenyl)acetic acid in 800 g chlorobenzene (or a reaction mixture of 1 mol bromo-(4-chlorophenyl)acetic acid/acid chloride described in Example 15a) is added through a dropping funnel over 2 hours The reaction mixture is kept for another 1-2 hours, until the conversion of bromo-(4-chloro-phenyl)acetic acid is complete. The reaction mass is diluted with 500 ml water and the pH is adjusted to 0.5 with hydrochloric acid at 35-40° C. The aqueous phase is separated from the organic product phase and then 800 g chlorobenzene are distilled off under vacuum at 90-100° C. The remaining chlorobenzene solution contains 218 g (4-Chlorophenyl)-prop-2-ynyloxy-acetic acid by LC analysis (yield=97% of theory based on bromo-(4-chloro-phenyl)acetic acid). The chlorobenzene solution of (4-Chloro-phenyl)-prop-2-ynyloxy-acetic acid can directly be used in the next step.

The "propargylacid" (4-Chloro-phenyl)-prop-2-ynyloxy-acetic acid can be isolated partly by concentration to a 50% solution and crystallisation/filtration at 0° C. About 170 g of (4-Chloro-phenyl)-prop-2-ynyloxy-acetic acid can be isolated in a crystallised form. Melting point=69-70° C.

EXAMPLE 15

Bromo-(4-chloro-phenyl)-acetic acid (Compound of formula VIII)

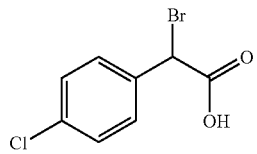

In a stirred reactor with reflux condenser (connected to a caustic scrubber) 171 g 4-chlorophenyl acetic acid are pre-charged in 750 g chlorobenzene and 41 g phosphortrichloride (0.3 Mol) are added. The mixture is heated to 100-110° C. and 280 g bromine (1.75 mole) are added within 1 hour through a dropping funnel. The reaction mixture is stirred for another 3-4 hour at 110-115° C. until the conversion of the 4-chlorophenyl acetic acid is complete (control by LC). The reaction mixture is cooled to 50° C. and 100 ml water is added. Excess bromine is destroyed by addition of NaHSO$_3$ solution. The reaction mixture is adjusted to pH 1 with aqueous NaOH solution and then the organic product phase is separated from the aqueous phase. The chlorobenzene phase contains 237 g bromo-(4-chloro-phenyl)acetic acid by LC analysis (yield=95% of theory based on 4-chlorophenylacetic acid). The "bromoacid" bromo-(4-chloro-phenyl)acetic acid can be isolated partly by concentration to a 50% solution and crystallisation/filtration at 0° C. About 200 g of bromo-(4-chlorophenyl)acetic acid can be isolated in a crystallised form. Melting point=92-93° C. $^1$H-NMR (CDCl$_3$) δ (ppm): 5.3 (s, 1H); 7.4 (4H, Ar); 9.7 (1H, OH)

EXAMPLE 15a

Bromo-(4-chloro-phenyl)-acetic acid (Compound of formula VIII)

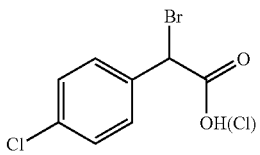

In a stirred reactor with reflux condenser (connected to a caustic scrubber) 171 g 4-chlorophenyl acetic acid are pre-charged in 400 g chlorobenzene and heated to 105° C. Within 30 minutes 42 g thionyl chloride is added at 105-110° C. to form partly the acid chloride. To the reaction mixture 256 g bromine (1.6 mole) are added within 90 minutes at 105-108° C. The reaction mixture is stirred for another 2-3 hour at 105-108° C. until the conversion of the 4-chlorophenyl-acetic acid is complete (control by HPLC). Excess bromine is distilled off as a bromine/chlorobenzene mixture at 90° C. until a vacuum of 250 mbar is reached and the colour of the reaction mixture has changed from brown to yellow. The bromine distillate can be re-used in the next batch. The reaction mixture, containing a mix of bromo-(4-chloro-phenyl)acetic acid and acid chloride is diluted with chlorobenzene to a weight of 800 g and can directly be converted to (4-chloro-phenyl)-prop-2-ynyloxy-acetic acid according to Example 14.

EXAMPLE 16

Bromo-(4-chloro-phenyl-acetyl chloride (Compound of formula XIII)

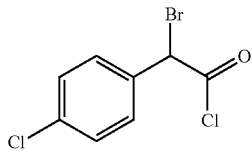

In a stirred reactor with reflux condenser (connected to a caustic scrubber) 171 g 4-chlorophenyl acetic acid (1 mol) are pre-charged into 600 g toluene and 7 g dimethyl-formamide. The mixture is heated to 50° C. and 125 g phosgene is introduced subsurface over 2-3 hours. The toluene is distilled off completely under vacuum and to the residue of 4-chlorophenyl acetic acid chloride 226 g bromine is added at 90° C. within 1-2 hours. For complete conversion the reaction mixture is stirred for another hour and then vacuum is applied to remove excess bromine. The orange residue of 290 g contains about 260 g 4-chlorophenyl-bromoacetic acid chloride (97% of theory, based on 4-chlorophenyl acetic acid), determined as methyl ester derivate by GC analysis.

$^1$H-NMR (CDCl$_3$) δ (ppm): 5.7 (s, 1H); 7.4 (s, 4H, Ar)

EXAMPLE 17

(4-Chloro-phenyl)-prop-2-ynyloxy-acetic acid prop-2-ynyl ester (Compound of formula III)

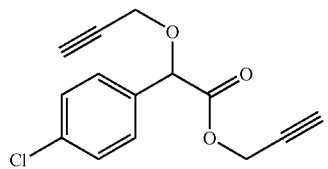

To a mixture of 70 ml propargylalcohol and 35 ml N-ethyldiisopropylamine 14 g of bromo-(4-chlorophenyl)acetyl chloride is added within 15 minutes at 0-5° C. to form a compound of formula VII. The reaction mixture is then heated to 60° C. and stirred at this temperature for 8 hours to give the above compound of formula (III). The reaction mixture is discharged into 400 ml ice/water. The pH is adjusted to 3 with hydrochloric acid and the product is extracted 3 times with 100 ml diethylether. The combined extracts are dried over MgSO$_4$ and the solvent evaporated at 50° C. under vacuum. Residue 12 g brownish oil.

$^1$H-NMR (CDCl$_3$) δ (ppm): 2.45+2.55 (2s, HC≡); 4.2+4.7 (2q, CH$_2$); 5.3 (is, CH); 7.4 (4H, Ar)

EXAMPLE 18

4-(1-hydroxyacetonitrile)-2-methoxy-phenol (compound of formula (IVA)

A1. In a 1 litre round bottom flask 80 g (0.52 eq) 4-hydroxy-3-methoxy benzaldehyde (compound (IVB), vanillin) were suspended in 135 g of water at 5° C. Over 2 hours 90 g (0.64 eq.) of a sodium cyanide 35% solution and 78 g (0.68 eq.) hydrochloric acid 32% were fed in parallel controlling the pH at 6.5 and temperature at 5° C. At the end of the feed the suspension was stirred for 6-8 hours at pH 6.5 and 5° C. to complete the conversion of the reaction. Subsequently the pH was adjusted to 1-2 with HCl 32% followed by the addition of 160 g methyl tert-butyl ether (MTBE) to extract the cyanohydrin into the organic solvent. The two layer mixture was stirred at ambient temperature for up to 1 hour. After that the agitator was stopped to allow layer separation, the lower aqueous layer was separated and to the MTBE layer 0.8 g (0.01 eq.) chloroacetic acid were added to stabilize the cyanohydrin prior to solvent swap. The MTBE solution was distilled under reduced pressure at 40-60° C. (100-500 mbar) affording 93 g (94% isolated chem. yield) of compound (IVA) as a yellow oil or crystalline residue.

A2. In a 1 litre round bottom flask 100 g (0.64 eq) 4-hydroxy-3-methoxy benzaldehyde (compound (IVB), vanillin) are suspended in 165 g of water at ambient temperature. Subsequently the resulting suspension is cooled under good agitation to 15° C. and then stirred for 30 min. Then 130 g (0.8 eq.) of a sodium cyanide 30% solution and 130 g (0.4 eq.) sulphuric acid 30% are fed in parallel over 4-6 h controlling the pH at 6.0 to 6.5 and temperature at 15° C. At the end of the co-addition the reaction mass is allowed to stir until crystallization of the product takes place, from then on the suspension is stirred for 2 hours at pH 6.5 and 15° C. to complete the conversion of the reaction. Subsequently the pH is adjusted to ≤0.5 with the addition of approx. 2 g sulphuric acid 30% followed by the addition of 170 g methyl tert-butyl ether (MTBE). The product is extracted into the organic layer under stirring for 1 h at 25-30° C. After that the agitator is stopped to allow layer separation, the lower aqueous layer is separated and to the MTBE layer 1 g (0.01 eq.) chloroacetic acid are added to stabilize the cyanohydrin prior to solvent swap. The MTBE solution is then distilled under reduced pressure at 40-60° C. (100-500 mbar) affording 112 g (96% isolated chem. yield) of compound (IVA) as a yellow oil or crystalline residue.

A3 In a 1 litre round bottom flask 160 (1.03 eq) 4-hydroxy-3-methoxy benzaldehyde (compound (IVB), vanillin) are suspended in 160 g of water at ambient temperature. Subsequently 4 g methyl tert-butyl ether (MTBE) are added and the resulting suspension is cooled under good agitation to 15° C. The pH is then adjusted to 7.0 to 7.5 by adding approx. 4 g NaOH 10%. Then 85 g (1.26 eq) HCN 40% aqueous sol. is fed to the stirred vanillin/water slurry over 30-60 min. At the end of the HCN-addition (if required) the pH is adjusted to 6.5 either with sulphuric acid 20% or NaOH 10%. The reaction mass clears up rapidly and is then allowed to stir for 3 h at 15° C. and pH at 6.0 to 6.5. Usually during the stir period the product starts crystallizing from a clear solution—once crystallization has taken place the suspension is allowed to stir for 1-2 h to complete conversion of the reaction. Subsequently the pH is adjusted to ≤0.5 with the addition of approx. 3 g sulphuric acid 20% followed by the addition of 170 g methyl tert-butyl ether (MTBE). The product is extracted into the organic layer under stirring for 1 h at 25-30° C. After that the agitator is stopped to allow layer separation, the lower aqueous layer is separated and to the MTBE layer 1 g (0.01 eq.) chloroacetic acid are added to stabilize the cyanohydrin prior to solvent swap. The MTBE solution is then distilled under reduced pressure at 40-60° C. (100-500 mbar) affording 180 g (96% isolated chem. yield) of compound (IVA) as a yellow oil or crystalline residue.

B. A 50 ml round bottomed flask was fitted with a mechanical agitator, thermometer, condenser, vent-gas scrubber (1:1 1NaOCl:NaOH), and an inert atmosphere. A solution of HCN in tetrahydrofuran (THF) (17% w/w) was prepared prior to this experiment by known literature methods. Potassium hydroxide (0.026 g, 0.02 eq.) and hydrogen cyanide solution in THF (5.02 ml, 1.5 eq.) were charged to the reactor, followed by a further charge of THF (5 ml). Vanillin (3.07 g) was dissolved in THF (5 ml) and charged to the stirred reactor over several minutes. The reaction was stirred at ambient temperature for 3.5 hours (small amount of white solid in a pale yellow liquid), and then analysed by quantitative HPLC to determine the yield. Conversion 90%; yield 83%.

C. To a flask containing 8.5 g acetone cyanohydrin (1 eq) was added 15.2 g vanillin (1 eq) in portions over 1 h. After stirring for 1 h, 0.8 ml of 35% aqueous sodium cyanide solution was added (0.05 eq). The resulting mixture was left to stir at room temperature for 5 days before quenching by the addition of 75 g methyl tert-butyl ether (MTBE) and 9 g water. Analysis of the organic layer by HPLC indicated the formation of vanillin cyanohydrin in 36% yield, with unreacted vanillin the only other visible component.

EXAMPLE 19

4-aminoethyl-2-methoxy phenol (Compound of formula IV via intermediate IVA")

To a 300 ml pressure reactor was added 30 ml methanol and 31.1 g of 98% sulphuric acid (1.41 eq). A slurry of 3.8 g 5% palladium on charcoal catalyst (0.004 eq) in 10 ml of methanol was added, followed by a 10 ml methanol wash. With the reactor under 5 bar hydrogen pressure and while maintaining a temperature of 20-25° C., 100 g of 40% vanillin cyanohydrin solution in methanol (1 eq vanillin cyanohydrin) was fed over 4 h, followed by a 15 ml methanol wash. After 20 minutes stirring, the pressure was relieved and 75 ml water added. This mixture was stirred at 45° C. to dissolve the product and then the catalyst filtered off. The catalyst cake was washed with 3×25 ml water and these washes combined with the mother liquor to give a product solution of 315 g, containing 10.0% AE-phenol by HPLC (86% yield).

The invention claimed is:

1. A process for the preparation of a compound of formula (I)

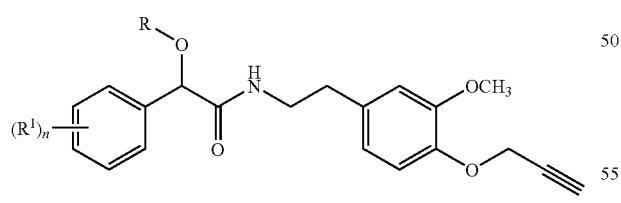

wherein:
R is an alkynyl group;
$R^1$ is alkyl, alkenyl, alkynyl, cycloalkyl, cycloalkyl-alkyl, phenyl and phenylalkyl, wherein each $R^1$ alkyl, alkenyl, alkynyl, cycloalkyl, cycloalkyl-alkyl, phenyl and phenylalkyl group is optionally and independently substituted with one or more halogen atoms; alkoxy; alkenyloxy; alkynyloxy; alkoxyalkyl; haloalkoxy; alkylthio; haloalkylthio; alkysulfonyl; formyl; alkanoyl; hydroxy; halogen; cyano; nitro; amino; alkylamino; dialkylamino; carboxyl; alkoxycarbonyl; alkenyloxycarbonyl; or alkynyloxycarbonyl; and n is an integer from 0 to 3, said process comprising:

(A) (i) the reaction of a compound of formula (III)

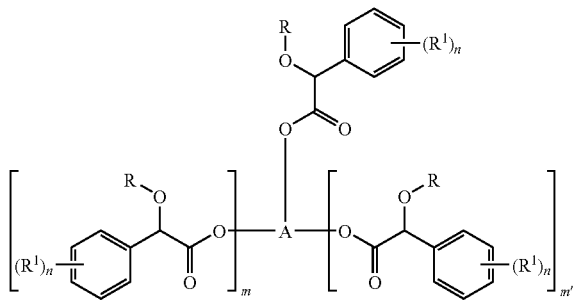

when one of m and m' is 0 and the other is 1, A is an alkanediyl, alkenediyl, or alkynediyl group containing at least two carbon atoms (and suitably having up to eight carbon atoms), optionally substituted by one or more groups independently selected from halogen, hydroxy, alkoxy, $C_{1-4}$ dialkylamino or cyano;

when m and m' are both 1, A is an alkenetriyl, alkenetriyl, or alkynetriyl group containing at least three carbon atoms (and suitably having up to eight carbon atoms), optionally substituted by one or more groups independently selected from halogen, hydroxy, alkoxy, $C_{1-4}$ dialkylamino or cyano;

and wherein if the group A contains three or more carbon atoms, one or more of the carbon atoms may optionally be replaced with an oxygen atom, provided that there is at least one carbon atom between any two oxygen atoms in the molecule with a compound of formula (IV)

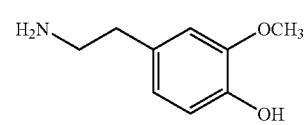

to give a compound of formula (II)

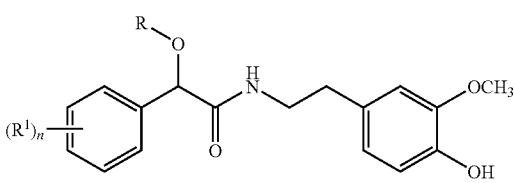

and (ii) the reaction of a compound of formula (II) with

to give the compound of formula (I).

2. A process according to claim 1, wherein R is ethynyl, prop-1-ynyl, prop-2-ynyl, but-1-ynyl, but-2-ynyl, 1-methyl-2-butynyl, hex-1-ynyl, 1-ethyl-2-butynyl or oct-1-ynyl.

3. A process according to claim 2, wherein R is prop-2-ynyl.

4. A process according to claim 1, wherein $R^1$ is 4-chloro, 4-bromo, 3,4-dichloro, 4-chloro-3-fluoro, 3-chloro-4-fluoro, 4-methyl, 4-ethyl, 4-propargyloxy, 3-methyl, 4-fluoro, 4-ethenyl, 4-ethynyl, 4-propyl, 4-isopropyl, 4-tert-butyl, 4-ethoxy, 4-ethynyloxy, 4-phenyoxy, 4-methylthio, 4-methylsulfonyl, 4-cyano, 4-nitro, 4-methoxycarbonyl, 3-bromo, 3-chloro, 2-chloro, 2,4-dichloro, 3,4,5-trichloro, 3,4-difluoro, 3,4-dibromo, 3,4-dimethoxy, 3,4-dimethyl, 3-chloro-4-cyano, 4-chloro-3-cyano, 3-bromo-4-methyl, 4-methoxy-3-methyl, 3-fluoro-4-methoxy, 4-chloro-3-methyl, 4-chloro-3-trifluoromethyl, 4-bromo-3-chloro, 4-trifluoromethyl, 4-trifluoromethoxy, 4-methoxy.

5. A process according to claim 4, wherein $R^1$ is 4-chloro.

6. A process according to claim 1, wherein n is 1.

* * * * *